United States Patent
Wiesel

Patent Number: 6,155,832
Date of Patent: Dec. 5, 2000

[54] METHODS AND APPARATUS FOR WHITENING TEETH

[76] Inventor: Peter E. Wiesel, 222 New Rd., Central Park East Suite 401, Linwood, N.J. 08221

[21] Appl. No.: 09/414,153

[22] Filed: Oct. 8, 1999

Related U.S. Application Data

[63] Continuation-in-part of application No. 09/205,220, Dec. 4, 1998.

[51] Int. Cl.$^7$ ..................................................... A61C 5/00
[52] U.S. Cl. ........................................... 433/215; 433/216
[58] Field of Search ................................... 433/215, 216, 433/29, 229, 80

[56] References Cited

U.S. PATENT DOCUMENTS

| | | | |
|---|---|---|---|
| 5,326,685 | 7/1994 | Gaglio et al. | 433/215 |
| 5,785,527 | 7/1998 | Jensen et al. | 433/215 |
| 5,894,017 | 4/1999 | Sagel et al. | 433/215 X |
| 6,045,811 | 4/2000 | Dirksing et al. | 433/215 X |

*Primary Examiner*—Nicholas D. Lucchesi
*Attorney, Agent, or Firm*—Norman E. Lehrer

[57] ABSTRACT

Methods for whitening a person's teeth are disclosed. In a first embodiment, the steps include providing a carrier, such as a transparent tape, where the carrier contains a catalyst thereon, and preparing a mixture which includes an oxygen radical generating agent and a buffer. The mixture is then applied to the carrier and the carrier is applied to a person's teeth. The person's teeth are then exposed to a light source. In another embodiment of the present invention, the mixture may include an oxygen radical generating agent, a catalyst, and a buffer. The mixture is then applied to a carrier which is applied to the person's teeth. The person's teeth are then exposed to a light source. In yet another embodiment, a mixture of an oxygen radical generating agent, a thickening agent, and a buffer is prepared and applied to a carrier. The carrier is then applied to a person's teeth which are then exposed to a light source. This carrier may be covered with a layer of release paper prior to use and packaged in a sterile container. In another embodiment a carrier, similar in structure to the carriers described above, is provided. A mixture of bleaching agents, without a catalyst, is then applied to the carrier by the dentist. The tape is then applied to the patient's teeth which are then exposed to a laser light. In another embodiment a non-woven, porous material is used as a carrier. The carrier is dipped into a teeth whitening mixture and then is applied to a person's teeth.

15 Claims, 2 Drawing Sheets

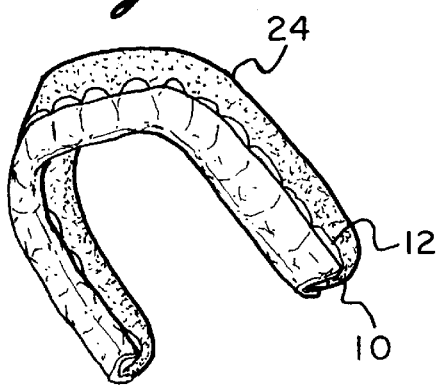
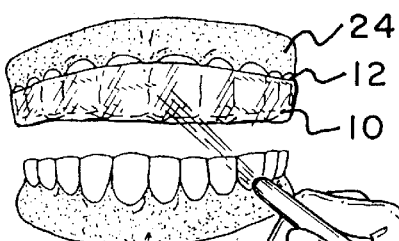
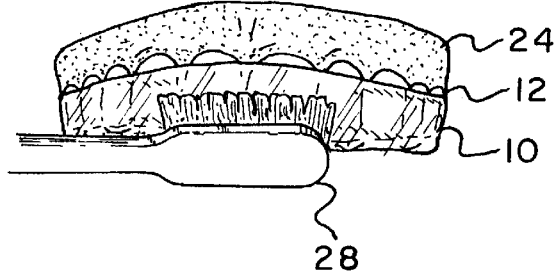
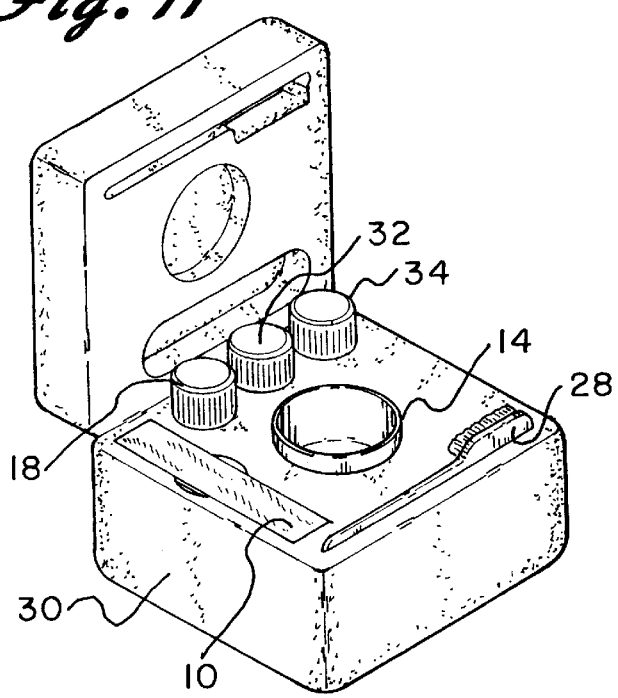
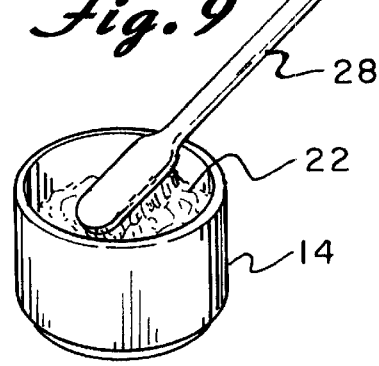

METHODS AND APPARATUS FOR WHITENING TEETH

CROSS-REFERENCE TO RELATED APPLICATION

This application is a Continuation-In-Part of co-pending U.S. application Ser. No. 09/205,220, filed Dec. 4, 1998.

BACKGROUND OF THE INVENTION

The present invention is directed toward methods and apparatus for whitening a person's teeth and more particularly, toward a method where a carrier has bleaching agents applied thereto and the carrier is applied to a person's teeth whereupon the teeth are exposed to a light source in order to enhance the effectiveness of the bleaching agents.

Dentists, like other health care professionals, often seek ways in which to improve instruments and procedures in order to provide better care for their patients. For example, dentists have experimented with various procedures for whitening teeth. One such procedure involves dipping a gauze strip into a bleaching material, applying the strip to a patient's tooth, and then exposing the covered tooth to a light source. This procedure, however, is not very effective because the amount of light which passes through the gauze strip is minimal since it is not transparent. A further limitation of this procedure is that because only one tooth is whitened at a time, the procedure is time-consuming, thereby increasing the patient's discomfort and exposure to the light source.

Currently, dentists whiten a patient's teeth by preparing a peroxide solution and coating the teeth with the solution. Once the solution is placed on the teeth, the teeth are exposed to a heat lamp or a laser light in order to heat the peroxide and to accelerate the bleaching process. In order to protect the patient's gums, a rubber sheet, Vaseline, or a light cured gel may be placed on the gums.

There are several disadvantages with the above-described process. For example, the rubber sheet placed over the patient's gums may stretch so that the peroxide solution leaks around the rubber sheet, exposing the patient's gums to the peroxide, thereby causing the patient discomfort. Also, this method cannot be performed on the upper set of teeth and the lower set of teeth simultaneously. Rather, only one set of teeth may be whitened at a time. Another disadvantage is that if a heat lamp is used a substantial amount of time is required in order to effectively bleach the teeth. Thus, the patient is exposed to the lamp for a great deal of time. This can cause extreme discomfort and inconvenience to the patient. Furthermore, the peroxide solution often times cannot be concentrated on the teeth. That is, the solution may drip off of the teeth if too much of the solution is applied or the solution may dry out if too little of the solution is applied.

Another method of whitening teeth is disclosed in U.S. Pat. No. 5,645,428 to Yarborough. This patent discloses using a laser light to activate bleaching agents applied to a patient's teeth. A mixture of peroxide and a first catalyst is prepared and then applied to the teeth. The teeth are then exposed to a laser light which activates the peroxide and catalyst to accelerate the bleaching process without heat. A second mixture of peroxide and a catalyst is then prepared and applied to the teeth. Again, the teeth are exposed to a laser light which heat activates the second mixture to accelerate the bleaching process. This process, however, increases the patient's exposure to laser light.

In yet another system, a peroxide solution may be combined with a gel which acts as a carrier. The mixture is then applied to a person's teeth which are then exposed to a light source. This system may be used by a person without the aid of a dentist or other medical personnel. That is, the peroxide-gel solution may be placed within a plastic mouthguard, such as shown in U.S. Pat. No. 4,990,089 to Munro, which is worn by a person overnight. A problem with this system is that the peroxide-gel solution decreases the effectiveness of the peroxide because generally these solutions are weak.

Also, the use of gel, in any dental office system, decreases the effectiveness of the peroxide because of the gel's opacity. That is, light is not able to pass through to all of the peroxide because of the opacity of the gel. Also, the gel prevents full contact of the tooth with the peroxide solution, thereby decreasing the effectiveness of the peroxide solution.

A home system for whitening teeth is disclosed in U.S. Pat. No. 5,891,453 to Sagel et al. The delivery system described in this patent comprises a strip of flexible material onto which the user may place a quantity of a tooth whitening substance. The flexible strip along with the tooth whitening substance is then placed on the surface of the teeth and is allowed to remain in place for a sufficient period of time to allow the active ingredient within the substance to act on the surface of the teeth. Because the system described in this patent is intended for home use, the concentration of the whitening substance must be relatively low and there is no suggestion of applying ultraviolet light or any other light in order to enhance the whitening function.

SUMMARY OF THE INVENTION

The present invention is designed to overcome the deficiencies of the prior art discussed above. It is an object of the present invention to provide a method for whitening a person's teeth which decreases the amount of time the person is exposed to a light source.

It is a further object of the present invention to provide a method of whitening teeth which is more efficient and less time-consuming than the methods currently being used.

In accordance with the illustrative embodiments demonstrating features and advantages of the present invention, there is provided a method for whitening a person's teeth which includes the steps of providing a carrier, such as a transparent tape, which contains a catalyst thereon, and preparing a mixture which includes an oxygen radical generating agent and a buffer. The mixture is then applied to the carrier and the carrier is applied to a person's teeth. The person's teeth are then exposed to a light source. In another embodiment of the present invention, the mixture may include an oxygen radical generating agent, a catalyst, and a buffer. The mixture is then applied to a carrier which is applied to the person's teeth. The person's teeth are then exposed to a light source.

In yet another embodiment, a mixture of an oxygen radical generating agent, a thickening agent, and a buffer is prepared and applied to a carrier. The carrier is then applied to a person's teeth which are then exposed to a light source. This carrier may be covered with a layer of release paper prior to use and packaged in a sterile container. This embodiment may be used by a person in his or her home without the aid of a dentist or any other medical personnel. In another embodiment, a carrier, similar in structure to the carriers described above, is provided. A mixture of bleaching agents, without a catalyst, is then applied to the carrier by the dentist. The tape is then applied to the patient's teeth which are then exposed to a laser light.

In a still further embodiment of the invention, a non-woven, porous material is used as a carrier. The carrier is dipped into a teeth whitening mixture or solution, which causes the same to become translucent, and is then applied to a person's teeth. Additional solution can be applied to the porous material while it remains on the patient's teeth.

Other objects, features, and advantages of the present invention will be readily apparent from the following detailed description of preferred embodiments thereof.

BRIEF DESCRIPTION OF THE DRAWINGS

For the purpose of illustrating the invention, there is shown in the accompanying drawings one form which is presently preferred; it being understood that the invention is not intended to be limited to the precise arrangements and instrumentalities shown.

FIG. 7 is a bottom perspective view of the carrier on a person's teeth;

FIG. 8 illustrates the step of exposing a person's teeth covered with the carrier to a light source;

FIG. 9 illustrates the step of placing a brush into the well containing solution;

FIG. 10 illustrates the step of applying more solution onto the carrier on a person's teeth; and FIG. 11 is a perspective view of an assembled kit of the present invention.

DETAILED DESCRIPTION OF THE PREFERRED EMBODIMENTS

Figure 1:
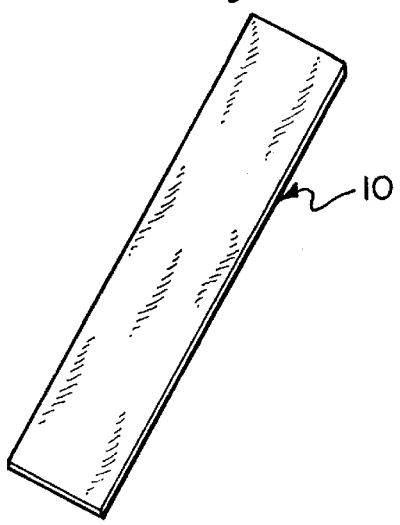
FIG. 1 is a perspective view of the carrier of one embodiment of the present invention.

A first embodiment of the teeth whitening method of the present invention essentially includes the steps of providing a carrier which may be, for example, a transparent tape or the like. The tape may have straight or scalloped edges in order to follow the contour of the gum line once the tape is adhered to a person' teeth as will be discussed in more detail below. The tape may be made from a biocompatible material and can be made in a variety of sizes and shapes to allow for the tape to fit over the teeth of a child, a teenager, or an adult.

A heat enhancer, catalyst, or any substance that causes a change in the rate of a chemical reaction without itself being consumed by the reaction is then applied to the carrier. The heat enhancer may be Beta carrotene, ferrous oxide, calcium chloride, or other similar types of catalysts. The catalyst may be coated onto or impregnated into the surface of the carrier. A mixture of bleaching agents is then applied to the tape by the dentist. The bleaching agents may be a mixture of an oxygen radical generating agent such as a peroxide and a buffer. The preferred peroxide is hydrogen peroxide although any peroxide selected from the group consisting of hydrogen peroxide, carbamide peroxide, calcium bicarbonate peroxide, sodium bicarbonate peroxide, and any other oxygen radical generating agent may be used. The preferred buffer is sodium hydroxide although any buffer selected from the group consisting of sodium hydroxide, sodium carbonate, sodium bicarbonate, calcium carbonate, calcium bicarbonate, potassium hydroxide, calcium hydroxide, and any other buffering agent may be used. A preferred ratio of hydrogen peroxide to sodium hydroxide is 35:5; however, this ratio may be varied as needed. Also, the concentration of the peroxide may vary, for example, a concentration between 30–50% may be used.

Once the patient's teeth are cleaned and prepared for the treatment, the tape, with the mixture thereon, is applied or unfolded onto the teeth with the scalloped edges of the tape fitting along the person's gum line. The mixture remains on the carrier and the carrier remains on the person's teeth due to surface tension. The heat enhancer reacts with the mixture of bleaching agents, creating heat and accelerating the otherwise slow bleaching effects of the peroxide. The person's teeth are then exposed to virtually any light source in order to further accelerate heating of the peroxide, thereby accelerating the bleaching of the teeth. The light source, for example, may be a heat lamp, a carbon dioxide laser, any short or long wave infrared laser, an argon laser, an utraviolet laser, or a Yttrium Arsenic Gallium (YAG) laser.

The second embodiment of the present invention is similar to the first embodiment; however, the carrier is not coated with a heat enhancer, rather, the enhancer is mixed with the oxygen radical generating agent and buffer. This mixture is then applied to the carrier surface and the carrier is applied to the person's teeth as in the first embodiment. Again, as in the first embodiment, the person's teeth are exposed to a light source which may be any of the sources discussed above. Also as in the first embodiment, the oxygen radical generating agent, buffer, and heat enhancer may be selected from their respective groups listed above. Furthermore, the carrier has scalloped edges and may be made from the same material and in the same sizes as described above.

In a third embodiment of the present invention, the carrier is coated with a thickened layer of the mixture containing an oxygen radical generating agent and a buffer. Also included in this mixture is a thickening agent such as silica dioxide. However, the thickening agent may be selected from the group consisting of silica dioxide, silicates, cellulose compounds such as hydroxyethylcellulose, lanolate, palmitate, oleate, sodium stearate, and other fatty acids. Alternatively, a substance containing sodium monoflurophosphate may be embedded into the carrier. In this embodiment, unlike the previous embodiments, release paper may be applied to the thickened layer, thereby covering the layer. The carrier may be stored in a sterile package in a rolled form or in differently sized strips. As in the previous embodiments, the oxygen radical generating agent and buffer may be selected from their respective groups as discussed above. Also, the carrier may scalloped edges and may be made from the same material and in the same sizes as described above. Furthermore, the back of the carrier may have designs thereon which appeal to children.

In order to use the device described in the third embodiment, a person removes the rolled carrier or tape from the package and unrolls as much of the tape as desired and releases the desired portion from the rest of the roll. Alternatively, if the tape is packaged in strips, the person simply removes the desired strip from the package. The person then removes the release paper from the tape and places or folds the tape against his or her teeth with the scalloped edges aligned with the gum line. The person may wear the tape throughout the day with the teeth being exposed to natural light. Thus, the person's teeth are whitened. Accordingly, a person may use the device without the aid of a dentist or other medical personnel.

In a fourth embodiment of the present invention, a carrier, having a structure as described above, is provided. A dentist may then prepare a mixture of bleaching agents, containing, for example, an oxygen radical generating agent and a buffer selected from the groups discussed. The dentist may then coat the carrier with the mixture. This embodiment, however, does not include a heat enhancer. Alternatively, the mixture may include just a peroxide solution, when the amount of bleaching is very light. The carrier is then placed on a person's teeth in the manner described above and the patient's are teeth exposed to a laser light source.

Figure 2:
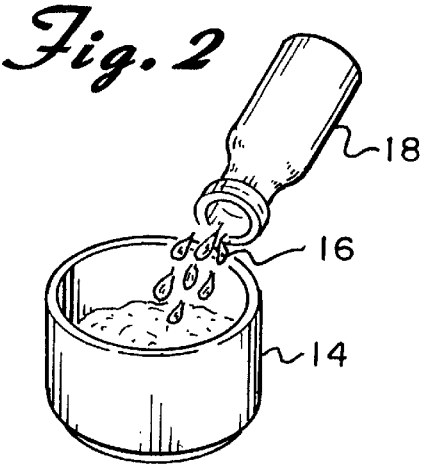
FIG. 2 illustrates the step of placing a whitening solution within a well.
Figure 3:
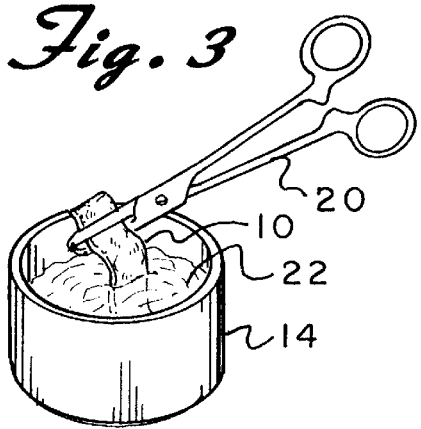
FIG. 3 illustrates the step of dipping the carrier into the well.
Figure 4:
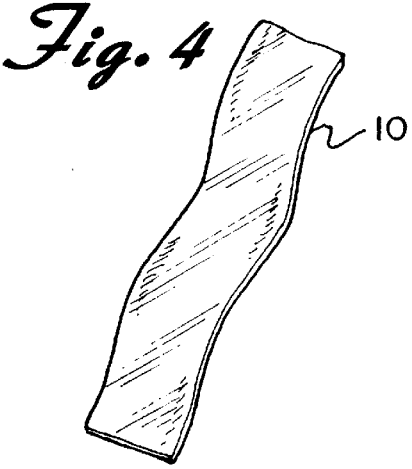
FIG. 4 is a perspective view of the carrier after it has been coated with the solution.
Figure 5:
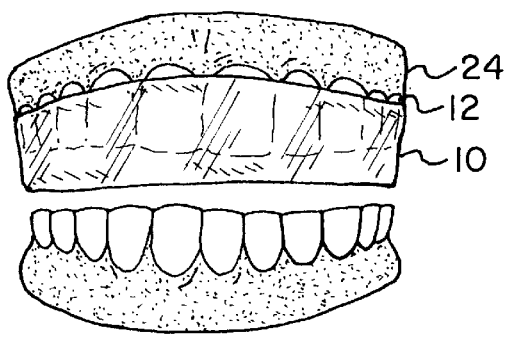
FIG. 5 is a schematic representation of the carrier being placed on a person's teeth.
Figure 6:
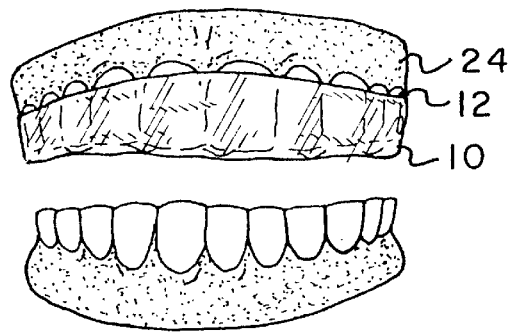
FIG. 6 is a schematic representation of the carrier covering a person's teeth before the actual whitening process begins.

A fifth embodiment of the present invention is shown in FIGS. 1–11. In this embodiment the carrier 10 is preferably in the form of a non-woven, porous, flexible material. (See FIG. 1.) The carrier 10 may be in the form of precut strips. The material is a high strength, lightweight, highly porous tissue which is made from a special blend of hemp and other selected cellulose fibers. The thickness of the material is approximately 60 microns and has a dry tensile strength of 2300 g/25 mm and a wet tensile strength of approximately 360 g/25 mm. The air permeability is approximately 1570 L/min/100 cm$^2$. This material is available from M&C Specialties Co. located in Southhampton, Pa. The material is generally opaque until it is wetted. When the material is wet, it becomes substantially translucent allowing light to pass therethrough. (See FIG. 4.)

In order to practice the method of this embodiment, the patient must first be protected. Cold cream or the like is applied to the patient's lower face, cheeks, chin, and below the nose areas. A retractor is used to pull back the cheeks and lips. Vaseline is then applied to the mucosa areas. Vaseline or a liquid dam is applied to the gingiva using a thin brush to reach the interproximal areas. Cotton rolls are inserted into the areas to be treated and a rubber dam may then be fastened to the teeth and gingiva.

The teeth 12 to be treated are cleaned using a mixture of pumice and 2% peroxide. The pumice is wiped down using only a dry piece of cotton. No water should be applied to the teeth at any time during the procedure. The carrier 10 is held up against the dental arch in order to see how much incisal overlap there is. Any incisal excess can be wrapped around to the lingual surface. (The same steps are followed for mandibular dentition treatments.)

In order to prepare the mixture or solution, a well 14 is partially filled with a peroxide 16, or any of the other bleaching agents discussed above, which may be stored within container 18. (See FIG. 2.) Approximately three drops of a heat enhancer solution is then placed into the well 14. The heat enhancer solution may also be any of the heat enhancer solutions discussed above. The desired strip 10 is picked up with college pliers 20 and is dipped into the well 14, thereby wetting the strip 10 with the mixture 22. (See FIG. 3.) The strip 10 should be moist but not dripping. The dentist then picks up the strip 10 at both ends and places the strip on the teeth 12, leaving at most, approximately a 1–2 mm gap between the gingiva 24 and the strip 10. (See FIG. 5.) The strip is maneuvered so that maximum coverage of the dentition is obtained. The remaining part of the strip is wrapped around the teeth to the lingual surface while gently pushing the strip into the interproximal areas. (See FIGS. 6 and 7.) A separate strip is used if lingual surface whitening is also to be performed. Alternatively, the strip may be cut so that only the front of the teeth are covered.

The applied strip 10 is then exposed to a light source 26. (See FIG. 8.) Different techniques, such as, applying energy to one tooth at a time or using an unfocused, more diffuse mode incorporating more teeth of the arch may be used. Also, the various light sources discussed above may be used in this embodiment. After approximately thirty seconds, a brush 28 is dipped into the well 14. (See FIG. 9.) The brush 28 may be an instrument with bristles such as shown or a cotton swab, or the like. Any excess solution is shaken off of the brush 28 and the solution remaining on the brush is applied to the strip that is in place and adhering to the dentition. (See FIG. 10.) The solution should not drip or run. The light source 26 is applied again. The brushing step is repeated for approximately 4–6 applications per arch, as necessary.

After the treatment has been completed, the strip 10 is removed from the arch and the teeth are wiped down with cotton. Fluoride gel is then applied with a burnishing instrument, such as a polishing cup. The patient should be advised that a whitening toothpaste should be used daily for at least one week. The patient should also be advised to refrain from ingesting highly staining beverages and foods as well as from chewing or smoking tobacco products for at least 24–48 hours.

In this embodiment a kit 30 is provided which houses the carrier 10. (See FIG. 11.) The carrier 10 may be packaged in a plurality of strips and in a variety of sizes. Alternatively, the strips may be cut by the dentist in order to fit the patient. The kit also includes containers 18, 32, and 34 for the bleaching agents and heat enhancing means discussed above. The well 14 or other means for the holding the bleaching agents and heat enhancing means is provided so that the strips may be placed therein, as discussed above. A cup or container may be substituted for the well so that the kit may be reusable. Brush 28 is also included for applying the bleaching agents and heat enhancing means to the carrier.

The present invention may be embodied in other specific forms without departing from the spirit or essential attributes thereof and accordingly, reference should be made to the appended claims rather than to the foregoing specification as indicating the scope of the invention.

I claim:

1. A method for whitening a person's teeth comprising the steps of:
   providing a carrier which includes a porous material that becomes at least translucent when wetted;
   providing a bleaching solution;
   applying said solution to said carrier;
   applying said carrier to a person's teeth; and
   exposing the person's teeth to a light source.

2. The method for whitening a person's teeth of claim 1 wherein said carrier is comprised of a non-woven fabric.

3. The method for whitening a person's teeth of claim 1 wherein said solution includes a heat enhancing means.

4. The method for whitening a person's teeth of claim 3 wherein said heat enhancing means is ferrous oxide.

5. The method for whitening a person's teeth of claim 3 wherein said heat enhancing means is calcium chloride.

6. The method for whitening a person's teeth of claim 1 wherein said bleaching solution comprises an oxygen radical generating agent and a buffer.

7. The method for whitening a person's teeth of claim 6 wherein said oxygen radical generating agent is a peroxide and said buffer is sodium hydroxide.

8. The method for whitening a person's teeth of claim 1 further including the step of applying an additional amount of said solution to said carrier while it is applied to the person's teeth.

9. A kit to be used for whitening a person's teeth comprising:
- a plurality of carriers in the form of strips of porous material;
- bleaching agents;
- heat enhancing means;
- means for holding bleaching agents and heat enhancing means;
- a well for preparing a mixture of said bleaching agents and heat enhancing means; and
- brush means for applying said mixture to said carriers.

10. The kit to be used for whitening a person's teeth of claim 9 wherein said carrier are comprised of a material that becomes translucent after said mixture has been applied thereto.

11. The kit to be used for whitening a person's teeth of claim 9 wherein said heat enhancing means is a catalyst.

12. The kit to be used for whitening a person's teeth of claim 11 wherein said catalyst is ferrous oxide.

13. The kit to be used for whitening a person's teeth of claim 11 wherein said catalyst is calcium chloride.

14. The kit to be used for whitening a person's teeth of claim 9 wherein said bleaching agents comprise an oxygen radical generating agent and a buffer.

15. The kit to be used for whitening a person's teeth of claim 14 wherein said oxygen radical generating agent is a peroxide and said buffer is sodium hydroxide.

* * * * *